US00PP36740P2

(12) United States Plant Patent
Knutson et al.

(10) Patent No.: US PP36,740 P2
(45) Date of Patent: Jun. 17, 2025

(54) SHRUB ROSE PLANT NAMED 'ARE24PMMN'

(50) Latin Name: *Rosa hybrida*
Varietal Denomination: ARE24PMMN

(71) Applicant: Heritage Legacy Partners, LLC, Brenham, TX (US)

(72) Inventors: Nathan Dennis Knutson, Brenham, TX (US); George Michael Shoup, Brenham, TX (US)

(73) Assignee: Heritage Legacy Partners, LLC, Brenham, TX (US)

( * ) Notice: Subject to any disclaimer, the term of this patent is extended or adjusted under 35 U.S.C. 154(b) by 0 days.

(21) Appl. No.: 18/806,077

(22) Filed: Aug. 15, 2024

(51) Int. Cl.
*A01H 5/02* (2018.01)
*A01H 6/74* (2018.01)

(52) U.S. Cl.
USPC ..... Plt./102

(58) Field of Classification Search
USPC ..... Plt./101, 102
See application file for complete search history.

*Primary Examiner* — Susan McCormick Ewoldt
(74) *Attorney, Agent, or Firm* — Koenig IP Works, PLLC; Katherine Koenig

(57) ABSTRACT

A new and distinct variety of shrub rose plant, referred to by its cultivar name, 'ARE24PMMN', is provided which abundantly and continuously forms clusters of small fragrant blooms. The growth habit is compact, full, and bushy. The foliage is smooth, matte, and dark green. The plant propagates from cuttings easily, has a reduced prickle count compared to most roses, blooms in clusters of small fragrant blooms. Flowers are light pinkish-white in cool temperatures and cream or eggshell white in warm temperatures. The new variety is well suited to growing in a container, hanging basket, or pot because of its compact and bushy nature.

3 Drawing Sheets

Genus and species: *Rosa hybrida.*
Variety denomination: 'ARE24PMMN'.

CROSS-REFERENCE TO RELATED APPLICATIONS

N/A.

ACKNOWLEDGEMENT OF FEDERAL RESEARCH SUPPORT

N/A.

BACKGROUND OF THE NEW VARIETY

The present invention relates to a new and distinct variety of shrub rose, botanically known as *Rosa hybrida*, and hereinafter referred to by the name 'ARE24PMMN'. Shrub rose is a member of Rosaceae.

The new variety of *Rosa hybrida*, and hereinafter referred to by the name 'ARE24PMMN', was created in Brenham, Texas, U.S.A. by artificial pollination wherein two parents were crossed, both of which having been previously observed, to reproduce their desired traits in the offspring. The female parent (seed parent) was the variety 'Peggy Martin' (not patented). The male parent (pollen parent) was the variety 'Marchéchal Niel' (not patented). Thus, the parentage of the new variety can be summarized as follows:

'Peggy Martin' x 'Marchéchal Niel'

The seeds resulting from the above pollination were stratified in an artificial environment and sown into trays in a greenhouse environment. Seedlings were obtained and displayed phenotypic and biological variation. Selective trialing and evaluation of the seedlings resulted in the identification of a single plant of the new variety.

The new shrub rose variety can be distinguished from its ancestors by inspecting the blossoming and growth habit. More specifically, the new rose has consistent blossoming during the growing season when compared to the female parent 'Peggy Martin', which only blossoms in the Spring and is followed up with a smaller blossoming in the Fall. The new shrub rose variety can also be readily distinguished from its ancestors upon observing the growth habit. More specifically, the new shrub rose 'ARE24PMMN' exhibits a rounded shrub growth habit, which is dissimilar to the parental varieties 'Peggy Martin' and 'Marchéchal Niel', which both exhibit a climbing growth habit.

Asexual reproduction of 'ARE24PMMN' was done by taking cuttings in Brenham, Texas, U.S.A. in beginning in 2019. Cuttings were taken from mature stems that were approximately 4 to 6 inches in length and approximately 0.25 inch in diameter. Initial cuttings were taken of the new variety and grew into mature plants. Subsequent cuttings were taken of the initial asexually reproduced plants and grown into mature plants. Mature plants of both the initially propagated plants and the subsequently propagated plants were compared. There was no observable difference between the generations. Therefore, it was demonstrated that the characteristics of 'ARE24PMMN' remain stable, uniform and true to type in successive generations of asexual reproduction.

Plant Breeder's Rights for this variety have not been applied for. The new shrub rose variety 'ARE24PMMN' has not been made publicly available more than one year prior to the filing of this application.

SUMMARY OF THE INVENTION

The new shrub rose variety 'ARE24PMMN' has not been observed under all possible environmental conditions. The phenotype of the new variety may vary with variations in environment and cultural practices such as temperature, light intensity, fertilization, irrigation, and application of plant growth regulators without any change in genotype.

The following traits have been repeatedly observed and are determined to be the unique characteristic of the new shrub rose variety. These characteristics in combination distinguish 'ARE24PMMN' as a new and distinct variety of shrub rose:

1. 'ARE24PMMN' is well suited for growing as an ornamental plant and source of fragrance in containers, hanging baskets, and as a landscape rose.
2. 'ARE24PMMN' abundantly and continuously forms small fragrant blooms.
3. 'ARE24PMMN' forms vegetation and stems that are lacking or have very few prickles.
4. 'ARE24PMMN' forms dark green, fine-textured foliage with a smooth finish.
5. 'ARE24PMMN' displays a compact, full, and bushy growth habit.
6. Flowers of 'ARE24PMMN' are light pinkish-white in cool temperatures (between approximately 33° F. and approximately 90° F.) and cream or eggshell white in warm temperatures (above approximately 95° F.).

Plant of the new shrub rose variety 'ARE24PMMN' differ from plants of the female parent, 'Peggy Martin' (not patented), in the following characteristics:

1. 'ARE24PMMN' features consistent blooming throughout the growing season, whereas 'Peggy Martin' blooms once in the spring and a few blooms in the fall.
2. 'ARE24PMMN' displays increased bloom fragrance.
3. 'ARE24PMMN' displays larger bloom size (approximately 1.75-2.0 inches) compared to the female parent 'Peggy Martin', which displays blooms having a diameter of approximately 1.5-1.75 inches.

Plants of the new shrub rose variety 'ARE24PMMN' differ from plants of the male parent, 'Marchéchal Niel' (not patented), in the following characteristics:

1. 'ARE24PMMN' displays increased disease resistance.
2. 'ARE24PMMN' displays compact rounded growth habit.
3. 'ARE24PMMN' displays increased bloom counts.

Plants of the new shrub rose variety 'ARE24PMMN' can be compared to plants of the variety 'The Fairy' (not patented). In side-by-side comparisons conducted in Brenham, Texas, plants of the new shrub rose variety 'ARE24PMMN' differed from plants of 'The Fairy' in the following characteristics:

1. Canes of 'ARE24PMMN' are nearly thornless compared to those of 'The Fairy'.
2. 'ARE24PMMN' displays blooms having a diameter of approximately 1.75-2.0 inches, whereas 'The Fairy' displays blooms having a diameter of approximately 1.0-1.25 inches.
3. 'ARE24PMMN' displays increased bloom fragrance compared to plants of 'The Fairy'.

Plants of the new shrub rose variety 'ARE24PMMN' can be compared to plants of the variety 'White Pet' (not patented). In side-by-side comparisons conducted in Brenham, Texas, plants of the new shrub rose variety 'ARE24PMMN' differed from plants of 'White Pet' in the following characteristics:

1. 'ARE24PMMN' displays larger and more vigorous, upright plant growth habit than plants of 'White Pet'.
2. 'ARE24PMMN' displays increased disease resistance.
3. 'ARE24PMMN' displays better asexual cutting propagation rate.

DESCRIPTION OF THE FIGURES

The accompanying photographs (as shown in FIGS. 1-3) illustrate the overall appearance of the new shrub rose variety 'ARE24PMMN'. These photographs show the colors as true as can be reasonably obtained in colored reproductions of this type. Colors in the photographs may differ slightly from the color values cited in the detailed botanical description, which accurately describe the colors of the new shrub rose variety.

Figure 1:
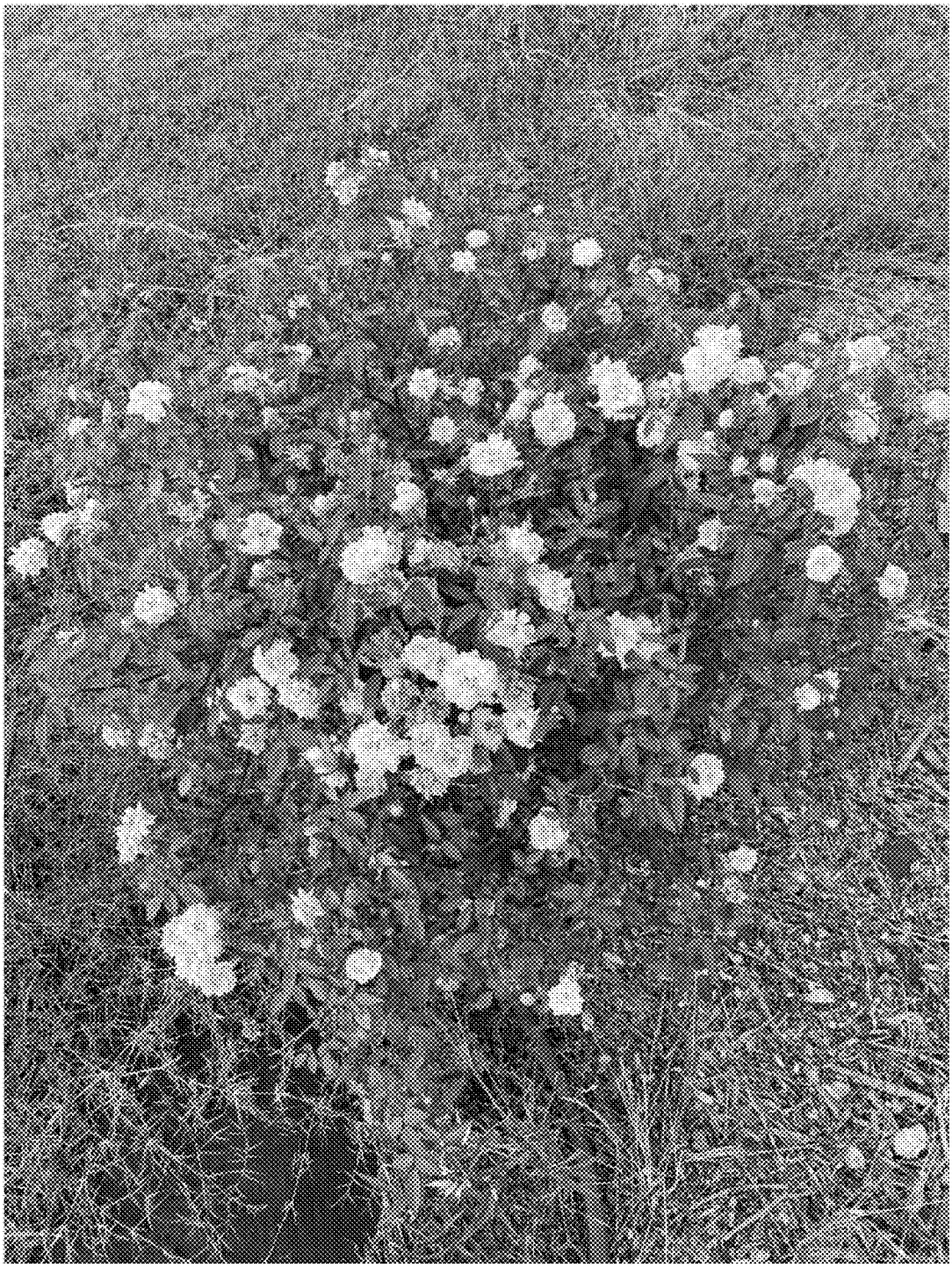
FIG. 1 shows a top perspective view of a typical flowering plant of the new shrub rose cultivar 'ARE24PMMN' to show its growth and branching habit, plant form, and flower color. The plant was grown in ground and is shown at 3 years old in full sun in Brenham, Texas. The plant was propagated from cuttings, container-grown in soilless media for 140 days, and then transplanted to the ground in September 2021. The photo was taken on Jun. 20, 2024.
Figure 2:
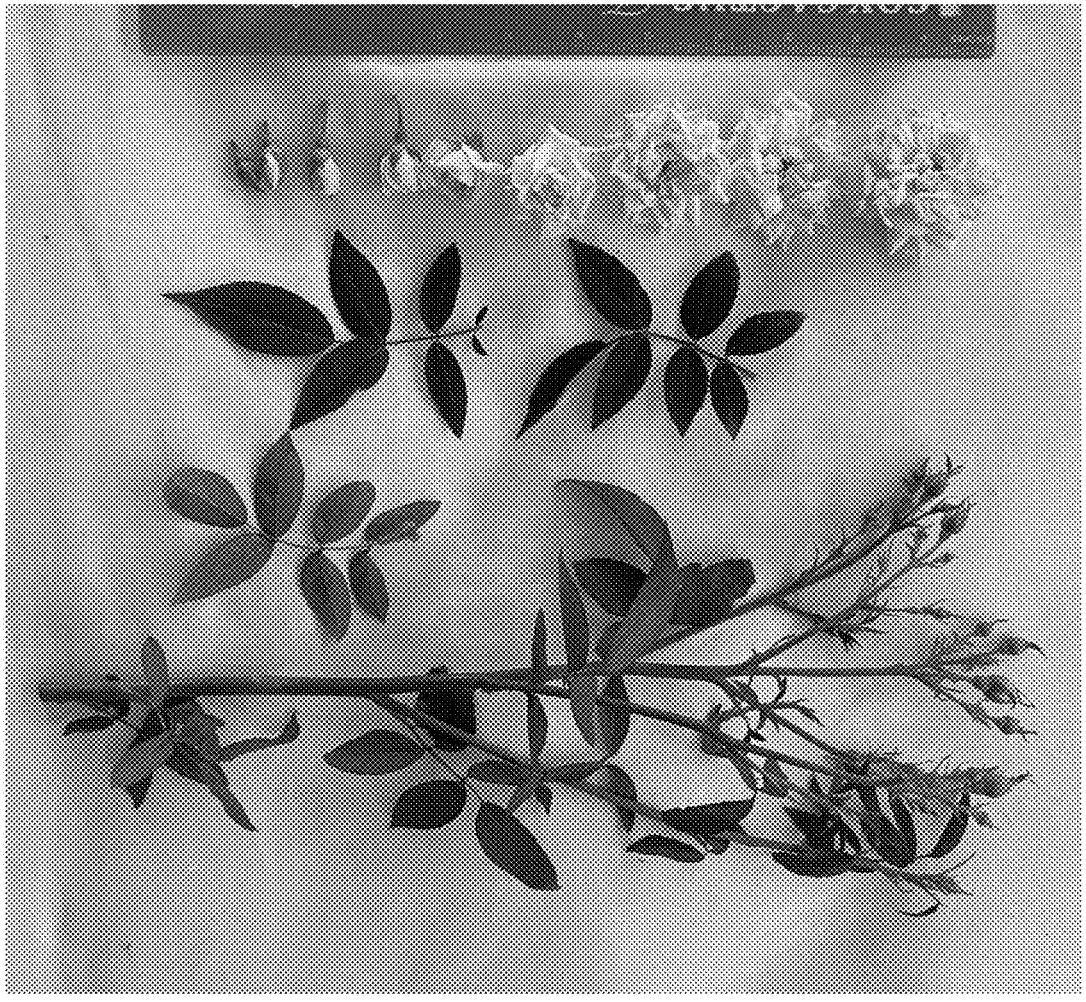
FIG. 2 shows a botanical view of a typical flowering plant of the new shrub rose variety 'ARE24PMMN' to show exemplary leaves, a branch, and flower form and color.
Figure 3:
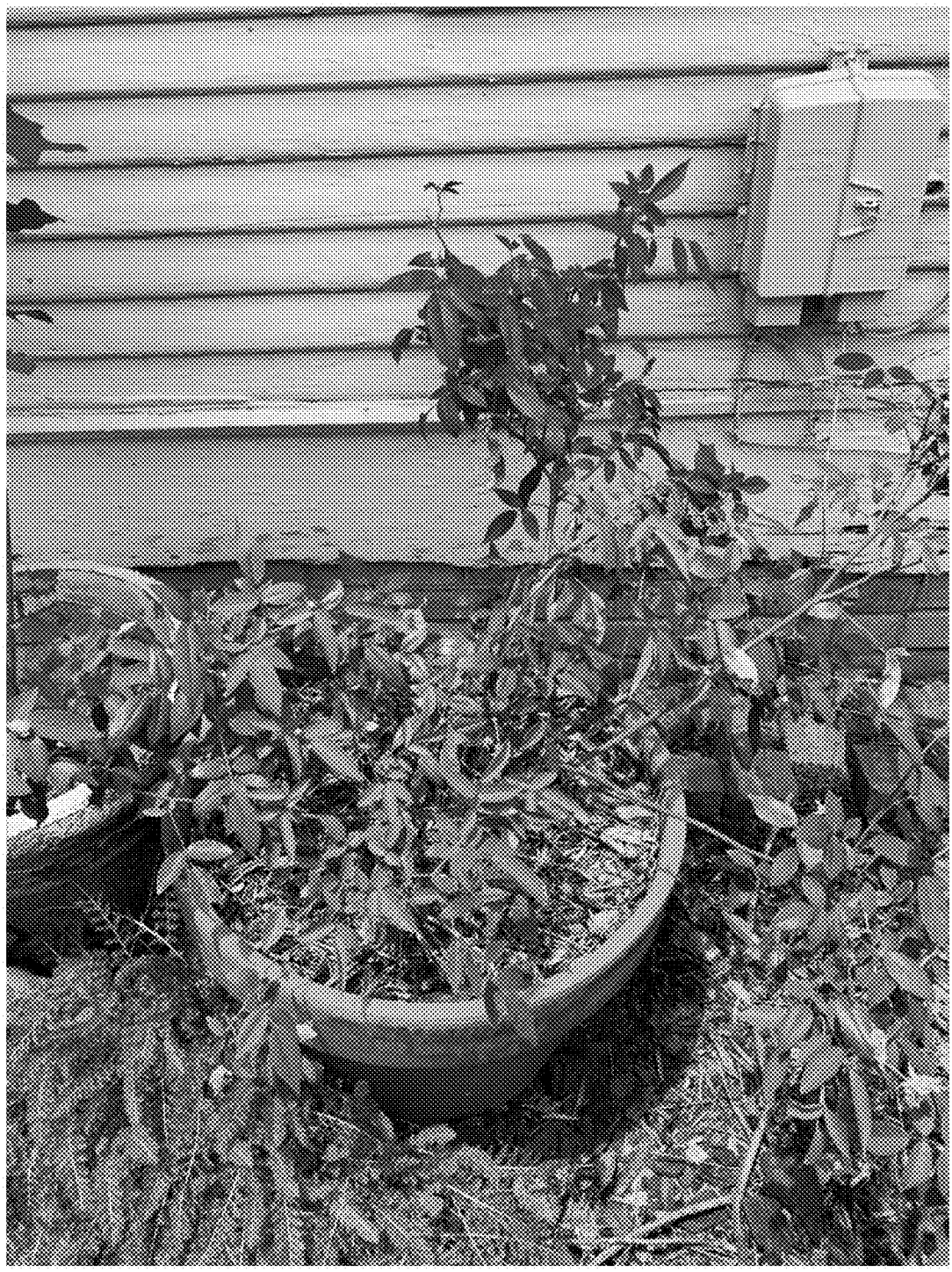
FIG. 3 shows a top perspective view of the new shrub rose cultivar 'ARE24PMMN' grown in an 18-inch container in full sun in Brenham, Texas.

The plants were propagated by cuttings, 2-gallon container-grown in soilless mix for 300 days, and then transplanted to the 18-inch container in the Fall of 2023. The photo was taken in Brenham, Texas on Jun. 23, 2024.

DETAILED BOTANICAL DESCRIPTION OF THE VARIETY

In the following description, color references are made to The Royal Horticultural Society (R.H.S.) Colour Chart, 1986 Edition, except where general terms of ordinary dictionary significance are used.

Botanical Description

Botanical classification:

*Family*.—Rosaceae.

*Botanical name*.—*Rosa hybrida*.

*Common name*.—Shrub rose.

*Variety*.—'ARE24PMMN'.

Parentage:

*Female or seed parent*.—'Peggy Martin'.

*Male or pollen parent*.—'Marchéchal Niel'.

Propagation:

*Type*.—Asexual reproduction done by stem cuttings.

*Time to initiate roots, summer*.—Approximately 3 weeks.

*Time to initiate roots, winter*.—Approximately 4 weeks.

*Time to develop roots, summer*.—Approximately 6 weeks.

*Time to develop roots, winter*.—Approximately 8 weeks.

Root description:

*Color*.—RHS 158D (Yellow-White Group).

*Rooting habit*.—Well rounded.

Plant description:

*Type*.—Landscape shrub rose.

*Growth habit*.—Compact rounded shrub with a full and bushy growth habit.

*Plant height*.—2 ft on average at maturity.

*Plant diameter*.—2 to 3 ft on average at maturity.

*Lateral branches*.—Length: 8 to 10 inches on average. Diameter: ⅛ to ¼ inch on average. Internode length: 1 to 1.5 inches on average. Texture: Smooth. Color, young: RHS 183A (Greyed-Purple Group). Color, woody: RHS 137B to 137C (Green Group).

*Stem*.—Quantity of main branches per plant: 3 to 4 on average. Quantity of leaves per branch: All leaves stem from lateral branches. Length of stem: 12 to 18 inches on average. Diameter: ½ to ¾ inch on average. Length of internodes: 2 inches on average. Texture: Smooth and slightly woody. Color: RHS 137B to RHS 137C (Green Group).

*Fruit*.—Rose hips (fruit) have not been observed.

Foliage description:

*Arrangement*.—Alternate, odd-pinnate, and compound.

*Length*.—1.25 inches on average.

*Width*.—0.5 inches on average.

*Shape*.—Ovate. Apex: Acute. Base: Obtuse.

*Margin*.—Serrate.

*Teeth along margins of leaf*.—35 to 40 on average.

*Texture, upper and lower surfaces*.—Fine and smooth.

*Luster*.—Upper surface: Slightly waxy. Lower surface: Matte.

*Color, developing and fully expanded foliage*.—Upper surface, developing: RHS 187A (Greyed-Purple Group). Upper surface, expanded: RHS 141A (Green Group). Lower surface, developing: RHS 183A (Greyed-Purple Group). Lower surface, expanded: RHS 138B (Green Group).

*Venation pattern*.—Reticulate.

*Color of veins*.—Upper surface: RHS 146A (Yellow-Green Group). Lower surface: RHS 147B (Yellow-Green Group).

*Petiole*.—Length: 1.5 to 2 inches on average. Diameter: 0.0625 inch on average. Color: Upper surface: RHS 146A (Yellow-Green Group). Lower surface: RHS 143C (Green Group).

Inflorescence description:

*Flower type*.—Very full, button eye, 80 petal count.

*Flowering habit*.—Repeat.

*Flowering longevity on the plant*.—3 to 5 days on average.

*Fragrance*.—Slight tea and rose aromas.

*Inflorescence diameter*.—3 to 3.5 inches on average.

*Inflorescence height*.—3 to 3.5 inches on average.

*Number of flowers per inflorescence*.—4 on average.

*Flower appearance*.—Very double, button eye.

*Flower diameter*.—1.75 to 2 inches on average.

*Flower buds* (*before showing color*).—Length: 0.5 inch on average. Diameter: 0.5 inch on average. Shape: Ovate with slight cresting of sepals. Color: RHS 156C to RHS 156D (Greyed-White Group).

*Bract*.—Length: 0.625 inch on average. Diameter: 0.1875 inch on average. Color: RHS 145C (Yellow-Green Group). Texture: Outer surface: Smooth. Inner surface: Smooth.

*Corolla*.—Arrangement/appearance: Very full, button eye, 80 petal count.

*Petal*.—Length from throat: Upper and lower petals: 0.875 inch on average. Width: Upper and lower petals: 0.5 inch on average. Shape: Apex: Obtuse. Margin: Entire. Color (shortly after bud opening): Warm temperatures (above approximately 95° F.): RHS 36D (Red Group). Cool temperatures (between approximately 33° F. to approximately 90° F.): RHS 62C (Red-Purple Group). Color (fully opened flower): Warm temperatures (above approximately 95° F.): RHS 158D (Yellow-White Group). Cool temperatures (between approximately 33° F. to approximately 90° F.): RHS 65D (Red-Purple Group).

*Calyx*.—Number of sepals: 5 on average. Length: 0.75 inch on average. Width: 0.25 inch on average. Shape: Acuminate. Apex: Appendiculate. Base: Truncate. Color: Apex: RHS 143C (Green Group). Base: RHS 143C (Green Group).

*Peduncles*.—Length: 1.75 to 3 inches on average. Diameter: 0.128 inch on average. Color: RHS 146C (Yellow-Green Group).

*Stamens*.—Quantity/arrangement: Sparse, 5 to 20 on average. Length of filament: 0.0625 inch on average. Color of filament: RHS 7C (Yellow Group).

*Anther*.—Shape: Ovoid. Length: 0.0625 inch on average. Color: RHS 14A (Yellow-Orange Group).

*Pistils*.—Quantity: 20 on average. Length: 0.128 inch on average. Stigma shape: Round. Color: RHS 22C (Yellow-Orange Group).

*Ovary color*.—RHS 143C (Green Group).

*Pollen*.—RHS 11A (Yellow-Orange Group).

Pest and disease resistance: The new shrub rose variety 'ARE24PMMN' displays moderate resistance to all tested races of black spot (*Diplocarpon rosae*), a good resistance to powdery mildew (*Podosphaera pannosa*), and a good resistance to downy mildew (*Peronospora sparsa*).

We claim:

1. A new and distinct shrub rose plant named 'ARE24PMMN' as illustrated and described herein.

* * * * *